US009935726B2

(12) United States Patent
Chi

(10) Patent No.: US 9,935,726 B2
(45) Date of Patent: Apr. 3, 2018

(54) SYNCHRONIZING WIRELESS DATA ACQUISITION OF PHYSIOLOGICAL INFORMATION

(71) Applicant: Yu Mike Chi, San Diego, CA (US)

(72) Inventor: Yu Mike Chi, San Diego, CA (US)

(73) Assignee: Cognionics, Inc., San Diego, CA (US)

( * ) Notice: Subject to any disclaimer, the term of this patent is extended or adjusted under 35 U.S.C. 154(b) by 201 days.

(21) Appl. No.: 14/760,554

(22) PCT Filed: Jan. 13, 2014

(86) PCT No.: PCT/US2014/011242
§ 371 (c)(1),
(2) Date: Jul. 13, 2015

(87) PCT Pub. No.: WO2014/110487
PCT Pub. Date: Jul. 17, 2014

(65) Prior Publication Data
US 2015/0358096 A1 Dec. 10, 2015

Related U.S. Application Data

(60) Provisional application No. 61/752,401, filed on Jan. 14, 2013.

(51) Int. Cl.
*H04J 3/06* (2006.01)
*H04W 56/00* (2009.01)
*H04W 4/00* (2018.01)
*H04L 29/08* (2006.01)
*H04W 84/18* (2009.01)
(Continued)

(52) U.S. Cl.
CPC .......... *H04J 3/0661* (2013.01); *H04W 4/005* (2013.01); *H04W 4/006* (2013.01); *H04W 56/0005* (2013.01); *A61B 5/0024* (2013.01); *G06F 19/363* (2013.01); *G16H 10/20* (2018.01); *H04L 67/12* (2013.01); *H04W 56/0055* (2013.01); *H04W 84/18* (2013.01)

(58) Field of Classification Search
CPC . H04J 3/0661; H04W 56/0005; H04W 4/006; H04W 4/005; H04W 84/18; H04W 56/0055; H04L 67/12; G06F 19/363; G06F 19/00; G06F 19/30; G06F 19/3406; G06F 19/3418; G06F 19/3443; G06F 19/3487; A61B 5/0024
See application file for complete search history.

(56) References Cited

U.S. PATENT DOCUMENTS 7,580,798 B2 * 8/2009 Brunner ................. A01K 1/031
382/110
7,777,622 B2 * 8/2010 Baldus ................. A61B 5/0002
128/903
(Continued)

*Primary Examiner* — Brian O'Connor
(74) *Attorney, Agent, or Firm* — Edward W. Callan

(57) ABSTRACT

A wireless data acquisition system includes a data acquisition unit including a data sensor; a first wireless data link and a second wireless timing link with predicable or low latency. Stimulus and time markers come from a trigger generator. Data signals from the data sensor are transmitted across the wireless data link and timing information of the data acquisition unit is transmitted across the wireless timing link. A receiving host receives the transmitted data and timing information for logging and/or processing.

5 Claims, 1 Drawing Sheet

(51) Int. Cl.
*G06F 19/00* (2018.01)
*A61B 5/00* (2006.01)

(56) References Cited

U.S. PATENT DOCUMENTS

| | | | | |
|---|---|---|---|---|
| 7,912,537 B2* | 3/2011 | Lee | A61N 1/37288 | 128/903 |
| 7,978,062 B2* | 7/2011 | LaLonde | A61N 1/37282 | 340/539.1 |
| 8,473,306 B2* | 6/2013 | Seely | A61B 5/412 | 600/300 |
| 8,538,528 B2* | 9/2013 | Von Arx | A61N 1/08 | 607/32 |
| 8,705,599 B2* | 4/2014 | dal Molin | A61N 1/37288 | 375/219 |
| 8,855,782 B2* | 10/2014 | Keenan | A61B 5/0031 | 607/31 |
| 9,089,276 B2* | 7/2015 | Xi | A61B 5/029 | |
| 9,210,358 B2* | 12/2015 | Griffin | H04W 88/06 | |
| 9,218,454 B2* | 12/2015 | Kiani | G06F 19/327 | |
| 9,485,345 B2* | 11/2016 | Dantu | H04M 11/04 | |
| 2008/0294020 A1* | 11/2008 | Sapounas | A61B 5/0024 | 600/301 |
| 2011/0032106 A1* | 2/2011 | Otto | A61B 5/0002 | 340/573.1 |
| 2013/0275159 A1* | 10/2013 | Seely | A61B 5/412 | 705/3 |
| 2015/0154364 A1* | 6/2015 | Biasi | G06F 19/3412 | 709/223 |
| 2016/0360965 A1* | 12/2016 | Tran | G06F 19/3418 | |

\* cited by examiner

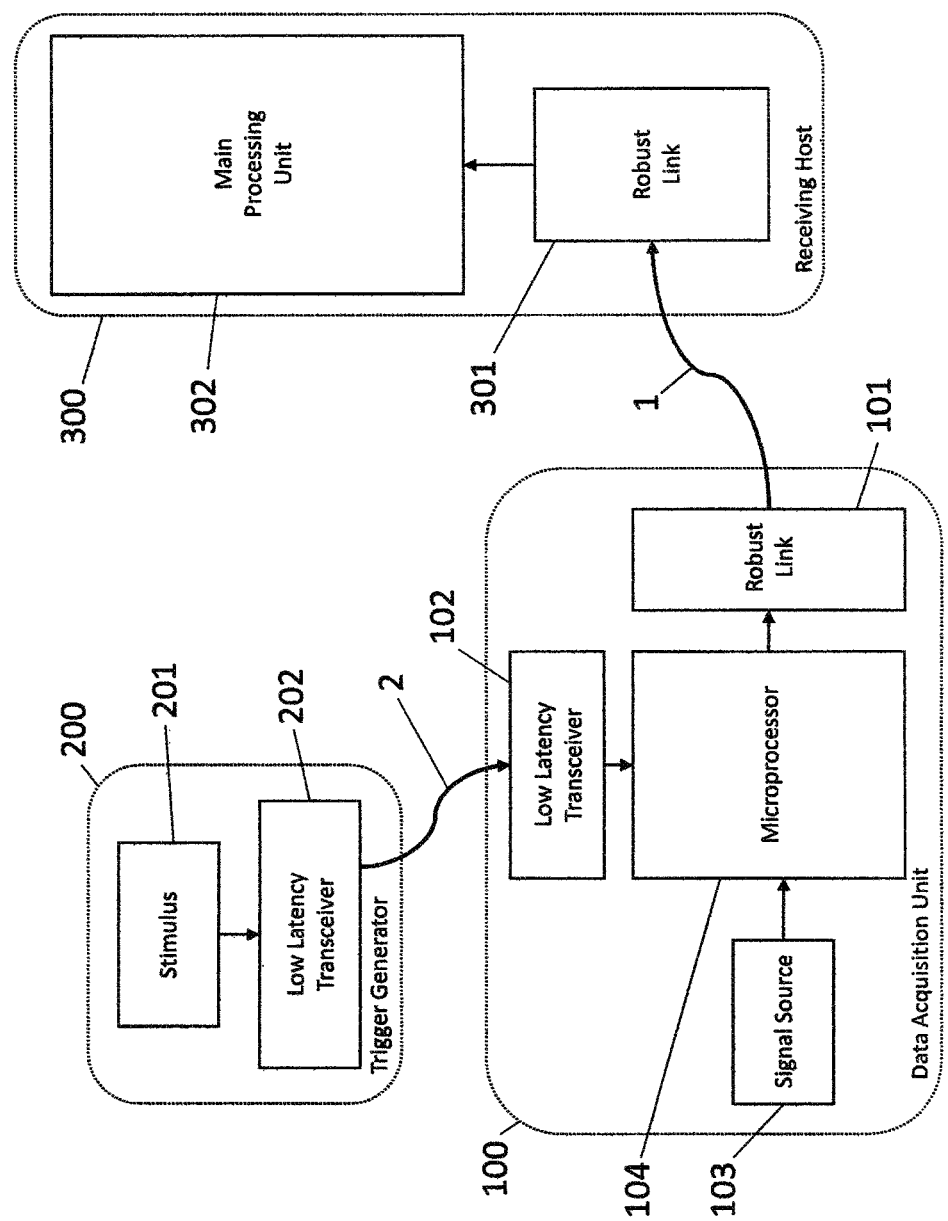

SYNCHRONIZING WIRELESS DATA ACQUISITION OF PHYSIOLOGICAL INFORMATION

This invention relates to time synchronization of data and events across wireless data links. In many fields involving medical or research collection of physiological data such as electroencephalograms (EEG), it is desirable to record data synchronized with some source of stimuli (e.g., auditory, visual, tactile). Latency between stimuli and data must be controlled since multiple trials are typically averaged together to produce useful information. Any mismatch between the actual onset of stimuli and the corresponding time marker in the collected data degrades the fidelity of the measurement.

In one example, an image is flashed on a screen and the subject's brain response recorded via EEG. The lag between screen flash and brain response is measured with millisecond accuracy. In a conventional setup, the screen producing the stimuli and the EEG system recording the response are wired together and no significant latencies due to data transmission are introduced. At the moment the screen flashes, a time marking signal is generated, fed into the EEG recording hardware. The EEG system then embeds the time marker within the EEG data stream that is transmitted or stored for subsequent analysis. The low latency of wired links allows for very precise marking of exactly when the event happened with respect to the EEG data stream, usually within a few, if not one, data samples.

More recently, significant interest has been generated in wireless data acquisition of physiological information such as EEGs. Compared to wired systems, wireless telemetry introduces a significant, unknown, and often unpredictable time delay between the stimulus and the recording of the subject's response. The reason is that current wireless protocols such as Bluetooth or WiFi, in order to be robust against data loss, add significant overhead in the form of checks and redundancy leading to delays between transmission and reception of the data, known as latency. The actual latency depends heavily on the transmission protocol, processing power and the amount of environmental interference. In a wired system, latencies are usually only a few milliseconds but wireless systems have latencies in the 10's or even 100's of milliseconds.

Wireless transmission also adds significant variable latency, known as jitter. This arises mainly from the fact that transmission of data across a wireless link is not guaranteed—interference is unpredictable and a wireless protocol must be prepared to buffer and retry as necessary to ensure that the data is eventually sent successfully. The amount of jitter can be in the 10's or 100's of milliseconds, especially for data oriented protocols such as WiFi or Bluetooth.

The combination of fixed latency and variable jitter introduced by typical wireless links is unacceptable for many precision physiological measurements, such as evoked potential responses (ERP). The sample rate for physiological signals is 200 or more samples/sec. Latencies, and especially jitter, that are greater than a few sample periods (10 ms) will compromise the ability to synchronize physiological measurements with stimulus, leading to data that is unusable. Therefore, we define 'low-latency' as a combination of fixed latency and jitter that is less than 10 ms. The problem is that the combination of latency and jitter make it impossible to determine exactly where the time markers from external stimuli match with the samples of the EEG data stream.

Traditional wired links exhibit low latencies and exhibit a predictable delay and jitter. As an example, transmitting one byte across a 57,600 bps UART takes exactly 156.52 microseconds (8 data bits+1 stop bit). Normally no re-transmissions are needed, but if an error correction protocol was added that had a maximum retry of 3 attempts, then the total possible latency is 468.75 microseconds, still under 1 sample rate of signal. An ideal wireless method should achieve both low latency and predictability.

It is worth noting, for clarity and scope, that other element in the data path, particularly a general-purpose computer, can add significant jitter and latency due to the overhead from an operating system. This is inherent in any system (wired and wireless) and outside the scope of the invention. Rather, the invention focuses on the transmission of accurate timing markers at the point the marker becomes a physical signal (e.g., an electronic pulse on a parallel port) to the data acquisition system. It is intended as a replacement for traditional wired links such as, but not limited to, the serial ports and parallel ports used by current instrumentation.

The simplest method to circumvent latency issues is to add a local trigger input to the wireless data acquisition unit. Triggers from stimuli can be accurately captured via an error-free wired port and embedded in the data stream with fidelity equivalent to traditional systems. However, the introduction of a dedicated wired port on the data acquisition unit defeats many of the advantages of wireless systems such as unrestricted mobility and essentially converts a wireless system into a wired one. In addition, the wired port creates a potential for unsafe electrical shocks unless designed with the same complex power isolation circuits used in traditional devices.

More sophisticated methods of synchronization involve developing custom or semi-custom protocols for the transmission of data. To avoid the latencies in standard protocols such as WiFi or Bluetooth, it is possible to build a custom wireless protocol between data acquisition unit and host. Running the software for the protocol on embedded microprocessors eliminates many of the timing uncertainties with software running on multitasking computers (e.g., PCs or tablets) and the protocol can be tailored to guarantee transmission within a certain interval or just skip to the next packet. This approach can generally work well but the data link will necessarily be less reliable than traditional protocols such as WiFi or Bluetooth. The greatest drawback, however, is the need for fully custom hardware, making the system incompatible with most PCs, tablets and other mobile devices (which only have standard transceivers built in) unless specialized receiver hardware and drivers are available for the host. This makes the approach impractical for many applications where the intended host is a mobile device such as a tablet or a phone.

Another approach is a semi-custom wireless protocol based on an existing standard such as Bluetooth. In this method, the data acquisition unit uses a standard wireless link. A custom receiver, e.g., embedded in a USB dongle, is used where the receiving software operates, like before, on an embedded microprocessor. Based on prior characterization, it is possible to align recorded data with stimuli from the host by predicting wireless latency and interpolating stimuli into the correct position in the received data. This approach is superior to a custom wireless protocol in that it allows the device to be compatible with many more devices (e.g., tablets and phones) without the need for custom receiver hardware. However the main drawback is that custom receiver hardware is still necessary if accurate timing performance is required, making the system still largely constrained to PCs and laptops that can support a custom receiver dongle. It is also worth noting that both custom and semi-custom protocol methods are inherently point-to-point between one wireless data acquisition unit and one host. In some applications it is desirable to broadcast time markers between a multiple of hosts and/or multiple wireless data acquisition units.

In light of these limitations, the current invention describes a set of methods to accomplish accurate time synchronization that is broadly compatible with any standard wireless protocol (e.g., Bluetooth, WiFi), on any receiving host without custom hardware and is capable of supporting multiple data acquisition units and hosts simultaneously.

The invention provides a wireless data acquisition system comprising: a data acquisition unit including a data sensor; a wireless data link; and a wireless timing link with predicable or low latency; wherein data signals from the data sensor are transmitted across the wireless data link and timing information of the data acquisition unit is transmitted across the wireless timing link.

The invention thereby provides at least two separate wireless paths between a wireless data acquisition unit and a receiving host. The first path is a robust link, typically with error correction, automatic re-transmission and high throughput capabilities for transferring the bulk of the data collected by the data acquisition platform. Because the first path is made to be resilient against error, the latency due to error correction and data processing overhead introduces a significant and non-deterministic latency in the data stream. The second path is a simpler wireless link with minimal error correction and is used primarily to transmit synchronization and timing markers between the data acquisition unit and the receiving host. Because the second path is simpler, the latency can be controlled to a greater degree of precision and time markers in the second path can be used to synchronize data/events between the data acquisition unit and host. Errors in the second path are relatively benign since they do not affect the actual data in the first path and lost timing can be recovered by interpolating from the time markers in the second path that are successfully transmitted.

FIG. 1 is a block diagram of an embodiment of a wireless data acquisition system according to the invention.

The system includes three main units, a data acquisition unit 100, a trigger generator 200 and a receiving host 300. The data acquisition unit 100 is the source of the measurements (e.g., EEG). Stimulus and time markers come from the trigger generator 200. A receiving host 300 receives the measurement data for logging and/or processing. Using a typical EEG application as an example to better illustrate these three components, the data acquisition unit 100 would typically consist of the EEG amplifiers and digitizers; the trigger generator 200 is the unit responsible for delivering stimuli (e.g., flashing light) along with trigger signals to mark the time location of such events; and the receiving host 300 would be a PC or laptop that records both EEG data with trigger makers.

It is important to note that the embodiment of FIG. 1 is shown as separate blocks only for purposes of clarity. As an example, the trigger generator 200 in many cases is the same physical device as the receiving host 300 (e.g., a computer delivering auditory stimuli). In other setups the triggers could come from a separate device (e.g., a tablet delivering a visual stimuli) but the overall data is aggregated at a PC elsewhere.

The wireless data acquisition unit 100 in the embodiment records a signal source 103 (e.g., EEG sensors) and has a microprocessor 104 and two wireless transceivers: 101—a robust link for data and 102—a low latency link for synchronization. The low latency transceiver 102 on the data acquisition unit 100 is connected to its matching transceiver 202 in the trigger generator 200. Information about the trigger events 201 delivered (e.g., time markers) are transmitted from transceivers 202 to 102 across the low latency link 2.

In general, there exist many methods to implement the wireless low latency link 2, including digital radio frequency modulation, analog radio frequency modulation, acoustic or light based methods. In some embodiments of the invention the low latency link 2 is implemented via infrared where 102 and 202 comprise a set of photodiodes. Infrared is simple, reliable, inexpensive and operates at the speed of light. The main drawback, however, is that infrared requires a direct line of sight, limiting the range of the technique. In other embodiments, the link 2 is radio frequency based. In one instance, a custom protocol based on 2.4 GHz digital modulation was used (Nordic nRF24L01+). The digital protocol allowed transmission of multi-bit trigger and synchronization codes, increasing the utility of the technique. Minimal error correction ensured a latency of less than 300 microseconds between the trigger generator 200 and data acquisition unit 100, well under one sampling interval of the signal source (EEG) 103.

The low latency of the link 2 allows for the microprocessor 104 to combine the signal source 103 and the stimulus 201 with a high degree of temporal precision—comparable to traditional wireline methods. The aggregated, time synchronized data is transmitted from the data acquisition unit 100 to the receiving host 300 across the wireless link 1 using transceivers 101 and 301. Data received by 301 is transmitted to the host's main processing unit 302 for further data analysis or storage. Since there now exists minimal latency constraints, the transceivers 101 and 301 can employ robust error correction to ensure wireless telemetry with minimal data loss. In some embodiments, the protocol across 1 is Bluetooth with 101 and 301 comprising Bluetooth transceiver modules. Other protocols are possible such as WiFi, a custom solution or a future wireless standard. In general, the optimal approach depends on the bandwidth desired, the power budget, system cost and compatibility with existing devices.

Although the embodiment of FIG. 1 shows the low latency link 2 between the trigger generator 200 and the data acquisition unit 100, it is worth noting that the invention more broadly encapsulates the key innovation of decoupling the transmission of latency-sensitive synchronization with error-sensitive data information by using more than one wireless link.

Many variations and alternative embodiments exist from the one shown in FIG. 1. As previously mentioned, it is possible to integrate the trigger generator 200 and receiving host 300 as a single unit. In the embodiment of FIG. 1, integration of time markers and signal was accomplished by the data acquisition unit 100 and then transmitted to the receiving host 300. Another embodiment of the invention could instead, integrate time markers with data on the receiving host 300 itself, the data acquisition unit 100 could transmit time markers to host on both the low latency link 2 and the resilient wireless link 1. The receiving host 300 would then integrate the data with it's own local events using the markers that exist in both data links. However, using the receiving host 300 to integrate timing with data is less optimal since it is usually a multi-tasking computer (e.g., tablet and phone) and will have an inherent non-deterministic latency in the software.

It is also possible to use the invention in applications involving multiple data acquisition units, multiple trigger generators and multiple receiving hosts. As an example, in a group EEG experiment, each subject would typically have their own data acquisition unit. One or more trigger generators would deliver stimuli to the subjects and transmit the time markers for these events via one or more low-latency links to each data acquisition unit. The time markers are integrated on each data acquisition unit and transmitted to one or more receiving hosts (e.g., a tablet computer for each subject). It is even possible to simply store the data on local memory on each data acquisition unit (e.g., on a flash memory card) and retrieved later for analysis.

Finally, although the described embodiments are focused on physiological measurements, particularly EEG applications involving synchronization of stimuli with data, the invention is broadly application to any field where wireless transmission of data with high timing accuracy is A system according to the invention can be used in a similar method to conventional wireline based methods. Data is collected from a subject and transmitted for storage and analysis. Time sensitive markers and synchronized with the data using the techniques described in the invention without wires. Compared to traditional systems, the lack of wire constraints between stimulus, data acquisition and host greatly increases the mobility of the setup. Using EEG as an example, the subject can freely move in an environment, opening up new possibilities for research and clinical applications.

The invention claimed is:

1. A wireless data acquisition system comprising:
a data acquisition unit including a data sensor;
a trigger generator for providing time markers;
a wireless data link for transmission of data acquired by the data acquisition unit; and
a wireless timing link with predicable or low latency of less than 10 ms;
wherein the data acquisition unit is adapted for receiving time markers for the data acquisition unit across the wireless timing link from the trigger generator and;
wherein the data acquisition unit is adapted for combining the time markers with the data signals acquired from the data sensor for transmission to a receiver across the wireless data link.

2. A wireless data acquisition system according to claim 1, wherein said wireless timing link comprises an infrared transceiver.

3. A wireless data acquisition system according to claim 1, wherein said wireless timing link comprises a radio frequency transceiver.

4. A wireless data acquisition system according to claim 1, wherein said wireless data link comprises a radio frequency transceiver.

5. A wireless data acquisition system according to claim 1, wherein the sensor is adapted for sensing physiological signals.

* * * * *